(12) United States Patent  (10) Patent No.: US 8,473,040 B2
Paul  (45) Date of Patent: Jun. 25, 2013

(54) ELECTROCARDIOGRAPHIC DEVICE AND METHOD

(75) Inventor: Fitzpatrick Adam Paul, Cheshire (GB)

(73) Assignee: Central Manchester University Hospitals NHS Foundation Trust, Manchester (GB)

( * ) Notice: Subject to any disclaimer, the term of this patent is extended or adjusted under 35 U.S.C. 154(b) by 55 days.

(21) Appl. No.: 12/811,632

(22) PCT Filed: Dec. 19, 2008

(86) PCT No.: PCT/GB2008/004188
§ 371 (c)(1),
(2), (4) Date: Jul. 2, 2010

(87) PCT Pub. No.: WO2009/087350
PCT Pub. Date: Jul. 16, 2009

(65) Prior Publication Data
US 2010/0292595 A1  Nov. 18, 2010

(30) Foreign Application Priority Data

Jan. 4, 2008 (GB) .................................... 0800144

(51) Int. Cl.
*A61B 5/02* (2006.01)
*A61N 1/00* (2006.01)
(52) U.S. Cl.
USPC .............................. 600/509; 607/36; 600/508
(58) Field of Classification Search
USPC .................................... 607/36; 600/508–509
See application file for complete search history.

(56) References Cited

U.S. PATENT DOCUMENTS

| 4,033,333 | A | 7/1977 | DeSalvo et al. |
| 4,432,367 | A | 2/1984 | Piesinger |
| 4,858,617 | A | 8/1989 | Sanders |
| 2004/0127802 | A1 | 7/2004 | Istvan et al. |

FOREIGN PATENT DOCUMENTS

| GB | 2431997 | 9/2007 |
| WO | 8805282 | 7/1988 |
| WO | 0042904 | 7/2000 |
| WO | 0074564 | 12/2000 |
| WO | 02096287 | 12/2002 |
| WO | WO 02096287 | * 12/2002 |
| WO | 2009087350 | 7/2009 |
| WO | 2009087350 A1 | 7/2009 |

OTHER PUBLICATIONS

International Search Report and Written Opinion of the International Searching Authority dated May 28, 2009, 13 pages.
European Search Report dated Mar. 17, 2008, 1 page.

* cited by examiner

*Primary Examiner* — Nicole F Lavert
(74) *Attorney, Agent, or Firm* — Bracewell & Giuliani LLP

(57) ABSTRACT

A hand-held device for acquiring electrocardiographic (ECG) signals from a patient comprises an electrode array with a gripping handle (15) and four electrodes (11-14). The electrodes typically form a quadrilateral array, the array being adapted for placement on the patients thoracic region without the need for upper clothing or underwear to be removed. The device can be used in a method to rapidly acquire ECG data relating to atrial fibrillation and/or flutter without the need for a conventional 12-lead ECG apparatus. The data can be transmitted to a computer for further manipulation and analysis. A kit for putting the method into effect includes the device, a means for communication with a computer and a computer program for running on the computer.

27 Claims, 1 Drawing Sheet

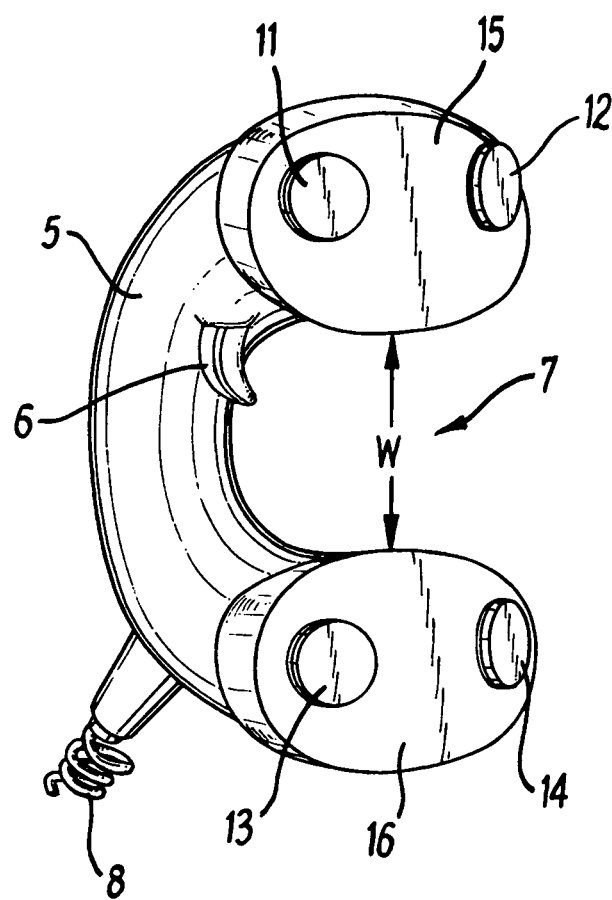

ELECTROCARDIOGRAPHIC DEVICE AND METHOD

RELATED APPLICATION

This application claims priority to PCT application PCT/GB2008/004188 filed Dec. 19, 2008, which claimed priority to British patent applications GB 0800144.8 filed Jan. 4, 2008.

The present invention relates to a hand-held device for obtaining electrocardiographic (ECG) signals from a patient. It is also concerned with a method for acquiring and manipulating an electrocardiographic dataset from a patient. In particular it is concerned with devices and methods suited to obtaining data which are useful for the diagnosis of atrial fibrillation and atrial flutter.

Electrocardiographic data is known to be of value for displaying the heart activity for individuals undergoing exercise training and for use in the diagnosis and treatment of medical conditions in patients. Conventional electrocardiograph machines are complex, costly and usually bulky pieces of apparatus which are operated by trained personnel, called cardiographers. As a result, their use has generally been restricted to hospitals, clinics and emergency medical vehicles. Recording a conventional 12-Lead ECG requires a subject to undress and lie down, and is time-consuming.

Atrial fibrillation is a medical condition that affects about 500,000 patients in the UK in 2007, most of whom are elderly, and the incidence is growing by around 5% per annum. It is detectable from a patient's electrocardiographic data. Atrial fibrillation is associated with more than 2.3 million admissions a year to hospital in the USA. The Framingham Heart Study reported that for patients with atrial fibrillation the risk of death in both sexes was double that for patients without atrial fibrillation, independent of age-group, over a 40 year follow-up period.

Health care costs for dealing with new cases of atrial fibrillation are very high. Atrial fibrillation also significantly affects quality of life and functioning for sufferers, so that there are further costs to society in terms of lost productivity and social costs.

Atrial flutter is another, closely-related, medical condition which is detectable from a patient's electrocardiographic data. In the UK, 50,000 new cases of atrial flutter are expected each year. Atrial flutter is easily cured by catheter ablation, but less than 2,000 such cases are undertaken in the UK each year, and atrial flutter patients typically become embroiled in a costly cycle of hospital admission, cardioversion and drug adjustment. Studies have shown that atrial flutter has a similar stroke-risk profile to atrial fibrillation, making it likely that improved services for curative atrial flutter ablation could reduce the morbidity, mortality and cost through reduced admission rates and stroke rates. One in three patients admitted to hospital with a stroke in the UK is in atrial fibrillation, and stroke is the greatest cause of morbidity, mortality and cost resulting from atrial fibrillation. There is also a causal relationship with heart failure and also increasingly with dementia, due to multiple small thrombo-embolic strokes.

Detection and treatment rates for atrial fibrillation are poor. Only 20% of eligible UK patients in permanent atrial fibrillation are currently (2007) being protected by appropriate anticoagulation with a drug treatment such as warfarin, before a stroke strikes. This poor rate of protection is due to poor rates of diagnosis. An estimated 150,000 people have a stroke in the UK each year. There are over 67,000 deaths due to stroke each year in the UK. If one in three stroke patients is in atrial fibrillation, and even if for only a third of these cases, atrial fibrillation is the cause of the stroke, then many strokes could be prevented by timely anticoagulation, which reduces the risk of stroke by 60%, leading to huge financial and social benefits. However, atrial fibrillation must be detected early, ahead of a stroke event, to achieve this.

Poor rates of diagnosis are due to atrial fibrillation often being asymptomatic when established, especially in the elderly, who are most at risk of stroke. Diagnosis is by analysis of electrocardiographic data. Asymptomatic atrial fibrillation patients will mostly be seen routinely or opportunistically by general practice doctors.

A recent project in the North West of England used 12-lead electrocardiograph apparatus in primary care for atrial fibrillation diagnosis, and found a very high detection rate when screening older patients. After the project ended, uptake and practice of the principles from the project in primary care were very poor, with little or no continuing activity. This reflected the difficulty of using conventional electrocardiograph technology for atrial fibrillation screening in GP practices. GPs have about 7-10 minutes per consultation, and it is estimated that at least 17 minutes are needed for undressing, laying the patient on a couch and wiring-up the ECG electrodes, entering patient's details, printing, and re-dressing, in routine 12-lead ECG recording. This does not include time spent by the GP in reporting and interpretation of the ECG, in which many GPs are not experienced.

A male doctor or nurse undertaking ECG recording may require a female chaperone for female patients because of the need for the patient to undress. Less than 30% of GP practices in the UK have their own ECG machine. Where they have a machine, they need to employ dedicated staff, and to identify space and time for ECG recording. This is costly and laborious, accounting for the current poor implementation. These difficulties greatly increase the chances of the rhythm changing, results going astray, or action not being taken in a timely fashion, or not being taken at all, given the pressures in GP practice.

An ECG rhythm-strip is adequate for the diagnosis of AF. However, using conventional ECG systems, even the recording of a 6-10 second rhythm strip requires a patient to lie on a couch and remove some clothing, and requires a GP to be trained and willing to do this in their consulting room as a screening routine after a pulse-check, and have a female chaperone present for female patients. It also requires each GP consulting room to be equipped with a conventional ECG machine. There are approximately 30,000 GP principles in the UK, and most have their own consulting room/office. Equipping GP's consultation rooms with conventional ECG apparatus would require a huge capital investment, which would probably be wasted, because the machines would be little used, for the reasons outlined above.

With a 12-lead ECG, not all the 12 leads are equally useful for confirming the diagnosis of atrial fibrillation, or its close cousin, atrial flutter. Atrial flutter has a similar stroke-risk to atrial fibrillation, is easily curable, and may give an apparently regular rhythm with a pulse-check. Similarly, atrial fibrillation that has a slow ventricular response rate may appear to be rather regular at a manual pulse-check. Maximum discriminative power for the diagnosis of atrial fibrillation and atrial flutter is given by ECG leads II, III and aVf in the frontal ECG plane, while leads V1-V6, (chest leads), in the horizontal ECG plane, add little discriminative power. However, even recording II, III and aVf with a conventional ECG apparatus still requires undressing and dressing and lying on a couch to record with available technology, and a chaperone where appropriate.

Even where a dedicated general practitioner would be prepared to prolong a consultation by 17 minutes to screen patients with suspected atrial fibrillation after a pulse-check, which might encompass 15% of a typical morning surgery of 30 patients, (i.e. add over an hour to the surgery), there is still much further work required to interpret the tracing, decide whether to refer the patient onward, and decide to whom this referral should be, and also to ensure that the ECG is appended to the patient's electronic record. The onerous nature of this process does not lend itself to enhanced screening of all elderly patients, for example, not least because their frailty makes them likely to require more time for the recording process.

In order for ECG-screening for atrial fibrillation diagnosis in primary care to be successful, for example in a mass-screening initiative of the over 65s, (who are at highest risk of atrial fibrillation related stroke, if not already prescribed warfarin), it has now been realised that a technology is required which:

i) is available to all GPs during a routine consultation in their individual room/office, ii) does not significantly prolong routine consultation time, i.e. takes 1-2 minutes, iii) does not have high disposable costs, so that GPs will use it readily with a low threshold for screening more of their patients, iv) requires minimal undressing/dressing, and would not require a male GP to have a chaperone in the room for the recording, which would be required if a female patient removed any clothing, especially underclothing, v) can be used with a sitting patient, or a patient in a wheel-chair, at the desk-side of the GP, without any major change in a patient's position, v) maximises discrimination of atrial fibrillation and atrial flutter by giving real or best approximate data from ECG vectors that constitute leads II, III and aVf, vi) enables the date and time-stamped ECG tracing to be appended to a patient's electronic GP record, vii) facilitates easy onward transfer of the ECG tracing for reporting, interpretation and patient-management without significant additional time or cost overhead, and viii) minimises the risk of delay, loss of data or inaction at any stage of the care-cycle.

Hence, now that this problem has been recognized, it is one object of the invention, amongst others, to provide a device and method for obtaining ECG data suitable for diagnosis of atrial fibrillation and/or atrial flutter, which overcomes some or all of the problems of the prior art. It seems that the technical barriers preventing rapid and convenient capture of atrial fibrillation and atrial flutter data by GP's in their consulting rooms has not previously been recognised in the prior art. If a patient was to be monitored by ECG by a doctor or consultant, it was accepted practice that a full ECG measurement should be taken using a conventional 12-lead machine.

U.S. Pat. No. 4,858,617 discloses a compact electrocardiograph device with three electrodes that are mutually spaced apart.

WO 88/05282 discloses a portable physiological monitor, which includes multi-functional electrodes to detect, inter alia, ECG signals, arranged in a planar triangular configuration.

U.S. Pat. No. 4,606,352 discloses a pocket-sized ECG monitor having three electrodes arranged in a line for placement against an patient's chest without the need for a paste or gel.

GB 2 431 997 discloses an EGC monitoring system in the form of a ball-shaped housing to be held in the hands of a subject.

U.S. Pat. No. 4,033,333 discloses an electrode arrangement in the form of a plate for use in taking electrocardiograms in an emergency when limited information must be taken rapidly. The arrangement consists of a small rigid plate having a triangular array of posts positioned thereon. The outer contour of the plate has the general shape of a "Y" for fitting between the breasts of an adult female patient.

It has now been found that a simple arrangement of electrodes on a small, portable, hand held device may be used to collect the necessary ECG channels for providing data from an individual which may be used for reliable diagnosis of atrial fibrillation and/or atrial flutter in that individual. It has also been found that signals needed for data relating to atrial fibrillation and/or atrial flutter in a patient can be obtained without need for a centrally positioned electrode in the electrode array. This allows for a design of device that may be used on a seated individual without the need for the individual's clothing to be removed, hence also potentially eliminating the need for a chaperone to be present for female patients.

Hence, a first aspect of the invention provides a hand-held device for acquiring electrocardiographic signals from a patient comprising a handle constructed and arranged for manual gripping of the device and an electrode array comprising four electrodes adapted for placement on said patients thoracic region whereby electrical contact may be made with said patient's mid-anterior thoracic skin for acquiring electrocardiographic signals through the four electrodes.

Preferably, one or more of the electrodes is oriented or orientable with respect to the hand-held device whereby contact with said mid-anterior thoracic region of said patient may be optimized.

By "orientable" it is meant that the angle between a surface of the electrode for contacting the patient's skin and the device may be varied, preferably by simply pressing the electrode into the patient's skin such that the surface of the electrode will orient to conform to the patient's skin at the locus of contact and thus provide good electrical contact. By "oriented" it is meant that the angle between a surface of the electrode for contacting the patient's skin and the device is selected to provide good electrical contact by conforming to a typical patient's skin at the locus of contact.

The device is for use with a seated or standing patient and the handle enables a medical professional to hold the device in place on a patient whilst measurements are taken.

A second aspect of the invention provides a method for acquiring and manipulating an electrocardiographic dataset from a patient comprising the steps of:

a) acquiring electrocardiographic signals from a patient by applying the electrode array of a hand-held device according to the first aspect of the invention to the thoracic region of a patient, b) capturing the electrocardiographic signals over a predetermined time period to form an electrocardiographic dataset, c) transferring the electrocardiographic dataset to a first computing means and d) adding patient identification data to the electrocardiographic dataset to form an identified electrocardiographic dataset.

Optionally the identified electrocardiographic dataset may be transmitted to a second computing means. This second computing means may be at a remote location.

A third aspect of the invention comprises a kit of parts comprising a device according to the first aspect of the invention, a data transfer means for transferring the electrocardiographic signals or the electrocardiographic dataset to a first computing means and a computer program adapted to run on said computing means and adapted to acquire and manipulate electrocardiographic data from a patient according to the method of the second aspect of the invention.

The features of the invention as detailed below are applicable to the first, second and third aspects of the invention.

The first computing means may be a part of the device itself, or may be a separate computing means, such as a computer, with which the device is in communication.

By "hand-held" it is meant that the device is of a suitable size such that it can be held and carried easily in a single hand of a human. This means that it will typically be less than 2 kg in weight and will have no linear dimension greater than 50 cm in length.

The contact electrodes of the electrode array are preferably firmly or orientably affixed directly to the device rather than loosely connected to the device by connecting wires or cables. The electrodes may be on the same surface of the device, or on different surfaces, but such that the electrodes are all substantially in the same plane on a first side of the device. This gives the advantage that electrical contact with a patient's skin can be made for all four electrodes of the electrode array by simply pressing the electrode array against the skin of the thoracic region of the patient, whilst the patient is seated, without removing any clothing, particularly underclothing.

The electrodes may be mounted on resilient, conductive mountings such that when the electrode array is pressed into the thoracic skin of the patient, the electrodes which make contact first may yield such that the other electrodes can be brought into good conductive contact with the patient's thoracic skin.

Preferably, each electrode is spaced from 4 cm to 20 cm from each adjacent electrode, more preferably from 5 cm to 10 cm, even more preferably from 6 cm to 8 cm. This provides for an adequate spacing between the electrodes to allow for a clear ECG signal to be measured for each ECG channel, whilst still allowing the electrode array to be sufficiently small to be placed onto the thoracic skin of a patient whilst that patient remains clothed.

Typically, the electrode array will be placed over the sternum of a patient. Because of the shape of the sternum region, it is preferable that the electrode surfaces are adapted to contact the skin at the thoracic region of a patient. For instance the electrodes to contact the breasts may be angled outwards such that their contact surfaces adapt to the skin surface of the breasts to provide good contact The electrodes may have flat planar contact surfaces or may have curved, convex contact surfaces in order to ensure good electrical contact with the thoracic skin.

Suitably, one or more of the electrodes, preferably all of the electrodes, is/are orientable with respect to the hand-held device whereby contact with said mid-anterior thoracic region of said patient may be optimized. For instance some or all of the electrodes may be pivotally mounted, for instance mounted in a ball and socket joint, on the device. This pivotal mounting should suitably be sufficiently firm such that the electrodes, after movement, remain affixed in their new position when placed against the thoracic region of a patient.

Preferably, the electrodes are resiliently mounted such that the electrodes may orient from a starting configuration to a contacting configuration when pressed against a patient's mid-anterior thoracic skin, returning to the starting configuration when the electrodes are taken away from the patient's skin.

In order to provide good electrical contact with the patient's skin, the electrodes suitably have a highly conductive and non-corroding surface, such as a gold or gold-plated surface adapted to make electrical contact with the patient's mid-anterior thoracic skin. This means that it will not be necessary to apply a conductive gel or paste to the patient's thoracic skin, thus minimising the time taken during a consultation, and minimising the time needed to clean the device between patients.

Preferably, all of the electrodes are orientable with respect to the hand-held device. The orientable mounts for the electrodes may be mounts which allow the electrodes to be re-oriented and remain in their new position (such as ball and socket joints) or may be resilient mounts such that the electrodes can adjust their angular position relative to the device as the device is pressed into the patient's thoracic skin to make electrical contact.

Preferably, the one or more electrode, is positioned on a surface of a deformable pad. The deformable pad, for instance, may comprises a flexible cover, such as a polymeric film or sheet, holding a viscoelastic gel such as a silicone gel. The electrode may be flush or substantially flush with the cover of the pad or stand proud of the cover of the pad. When the pad is pressed into the patient's thoracic skin, the pad may suitably deform such that the pad's skin will conform to that of the patient, bringing the electrode into good electrical contact with the patient's skin. Preferably, the pad and electrode(s) are arranged to be easily cleaned or sterilised by wiping the pad and electrode(s), for instance with a sterilising wipe. This enables the device to be cleaned between uses on different patients in order to prevent transfer of infection. Preferably, the cover of the pad is of a material which is resistant to bleach and/or oxidising agent and/or cationic disinfection agents. The electrical lead from an electrode to the device will typically pass through a sealed aperture in the cover of the pad and through the viscoelastic gel of the pad, with the electrode embedded in or adhered to the cover of the pad. Alternatively, the electrical lead may be located on the outside of the cover of the pad, connecting an electrode to the remainder of the device.

A preferred device comprises a first electrode housing carrying one or more of the four electrodes and a second electrode housing carrying one or more of the four electrodes, wherein the first and second electrode housings are constructed and arranged to be mutually spaced to provide a gap therebetween. Suitably, the gap is arranged to permit placement of the four electrodes onto the mid-anterior thoracic region of a patient whilst the patient is wearing a brassière. This is particularly useful for female patients as it allows measurements to be made by simply partially unbuttoning a blouse or shirt front whilst the patient continues to wear their brassiere.

Suitably, the gap is arranged to provide a void having width of at least 1 cm, preferably at least 2 cm between the first and second electrode housings, and a depth of at least 1 cm, preferably at least 2 cm from the patients skin when the four electrodes are positioned on said mid-anterior thoracic region of a patient.

The device may have an electrode array comprising four electrodes positioned substantially at the vertices of a quadrilateral, preferably a trapezium, more preferably a rectangle.

With such an electrode arrangement, the device suitably comprises a first electrode housing carrying a first pair of the four electrodes and a second electrode housing carrying a second pair of the four electrodes, wherein the first and second electrode housings are constructed and arranged to be mutually spaced to provide a gap therebetween.

Surprisingly, it has been found that adequate information for assessment of atrial flutter/fibrillation can be obtained from such a quadrilateral array of electrodes without the need for a traditional triangular electrode configuration with a central electrode positioned within the triangular array. This allows the device to be simplified and allows for considerable versatility in the manner of placement of the electrodes on the anterior skin of the thoracic region of the patient, depending upon the patient and their body shape.

For instance, the device may comprise an upper pair of electrodes for placement on the upper mid-anterior thoracic region, and a lower pair of electrodes for placement on the lower mid-anterior thoracic region, avoiding any need for contact with the cleavage region of the breasts of a female patient.

Suitably, the electrodes comprise a gold surface adapted to make electrical contact with said patient's mid-anterior thoracic skin.

Suitably, the device comprises an actuating means adapted to initiate capture of electrocardiographic signals over a predetermined time period onto a data storage means as an electrocardiographic dataset. The device may comprise a control system in the form of a microprocessor chip programmed to deal with the control of the functioning of the device and the acquiring of an ECG dataset. By ECG or electrocardiographic dataset is meant a set of ECG voltages for each of several ECG channels stored along with the corresponding time value for each voltage. Typically the dataset will be for a time period from 4 to 30 seconds, preferably 5 to 20 seconds. This provides sufficient information for the ECG dataset to be usable for diagnosis of atrial fibrillation and/or atrial flutter.

The various ECG channels correspond to the voltage differences measured along the different ECG leads. In the field of electrocardiography, the term "lead" has a special meaning. The usual meaning for ECG is an imaginary line or vector in the body along which the voltage difference is measured. The electrical activity of the heart generates a three-dimensional voltage field in the body, and this field can be sampled along specific vectors using the various leads of the ECG system.

A conventional 12-lead ECG has, in fact, only 10 electrodes contacting the patient's skin. The different lead descriptors relate back to the origins of ECG when patients placed their arms and legs in buckets of saline solution in order to obtain measurable voltages. Although buckets of saline solution are no longer needed, in conventional 12-lead ECG, electrodes are still placed on the arms and legs of a patient to mimic the original methodology. The first three leads (known as bipolar leads because they measure the voltage differences between two extremities) of the modern ECG system have lead I as the dipole from the right arm to the left arm of the patient, lead II as the dipole from the right arm to the left leg and lead III as the dipole from the left arm to the left leg.

The limb leads give data corresponding to the heart's activity in the frontal plane.

The leads aVr, aVl, and aVf (Goldberger's augmented leads) in a 12-lead system are known as the augmented limb leads. These unipolar leads are measured using the same three electrodes as leads I, II, and III for the positive electrode respectively. However, they view the heart's electrical activity along different vectors because the negative electrode in each case is formed by combining the signal from each of leads I, II, and III together to form a pseudo-electrode known as Wilson's central terminal.

The unipolar leads need to be amplified (hence the use of the term augmented) because the voltage differences measured by these unipolar leads are relatively small. This can be achieved by omitting the connection of the lead being measured to the central electrode, effectively doubling the signal.

Lead aVr or "augmented vector right" has the positive electrode on the right arm. The negative electrode is a combination of the left arm electrode and the left leg electrode, which "augments" the signal strength of the positive electrode on the right arm.

Lead aVl or "augmented vector left" has the positive electrode on the left arm. The negative electrode is a combination of the right arm electrode and the left leg electrode, which "augments" the signal strength of the positive electrode on the left arm.

Lead aVf or "augmented vector foot" has the positive electrode on the left leg. The negative electrode is a combination of the right arm electrode and the left arm electrode, which "augments" the signal of the positive electrode on the left leg.

Together with leads I, II, and III, augmented limb leads aVr, aVl, and aVf form the basis of the hexaxial reference system, used to monitor the heart's electrical activity in the frontal plane.

A set of 6 precordial (chest) leads is used in the conventional 12-lead system to monitor the heart's electrical activity in the horizontal plane.

It has now been found that the hexaxial signals required to monitor the heart's frontal plane electrical activity can be measured easily with a hand-held device employing four electrodes arranged in a quadrilateral array. Rather than providing a centrally positioned terminal, the presence of an independent fourth electrode allows for a good signal to be achieved using a small, portable device.

In order to monitor for signs of atrial fibrillation or atrial flutter, only the hexaxial signals of the frontal plane need to be monitored—the precordial electrodes for monitoring the horizontal plane are not needed. In fact, the three most important signals for monitoring atrial fibrillation or flutter are the leads II, III and aVf, though all of the hexaxial leads show flutter and fibrillation signals, when the conditions are present.

Although the device of the present invention may not necessarily provide horizontal plane information, by solving the problems of allowing accurate monitoring of horizontal plane activity in a brief consultation without the need for the patient to strip, the device provides considerable benefits; particularly in terms of screening for atrial fibrillation and atrial flutter using the hexaxial signals.

Suitably, the electrocardiographic dataset gathered by the device of the invention comprises six channels. These channels (by "channel" is meant a voltage/time dataset) suitably correspond to the six leads of the hexaxial system as detailed above (leads I, II, III, aVL, aVR and aVF).

When the device has a quadrilateral array, the hand held device is oriented on the thoracic region of the patient such that the quadrilateral electrode array of the hand-held device is oriented with two vertices of the quadrilateral situated lower on the patient's thoracic region than the other two vertices. The quadrilateral will typically be oriented with a first pair of electrodes aligned across the breast region (roughly normal to the spinal column of the patient) and the remaining second pair of electrodes below the first pair with the electrodes approximately on either side of the sternum of the patient, again aligned roughly normal to the spinal column. However, other electrode configurations and orientations may be employed and fall within the scope of the invention as defined by the claims.

The device itself may comprises a data storage means for recording the ECG data, or the data storage means may be part of a computing means, such as a local personal computer, with ECG data transferred from the device to a computing means. In either case, the device suitably comprises a data transfer means for transferring the electrocardiographic signals or the electrocardiographic dataset to a computing means.

The device may further comprise a display means adapted to instantaneously display electrocardiographic signals from the patient. Alternatively, the device may transmit the ECG signals to a local computer means where the signals may be displayed on a display means, such as a display screen, forming part of the local computing means. In either case, this allows the signal to be visually monitored, such that the person using the device can ensure that a stable, strong signal is being acquired prior to initiating capture of the electrocardiographic signals over a predetermined time period onto a data storage means as an electrocardiographic dataset.

Hence, in the method of the invention, a display means may be used to assess the quality of the electrocardiographic signal prior to initiating capture of the electrocardiographic signals over a predetermined time period to form an electrocardiographic dataset.

The operation of the device may be controlled by a computer program running on a microprocessor means on the device itself, or by a computer program running on a computing means to which the device is connected, or by a combination of two such computer programs interacting with each other.

The data transfer means may be a hard-wired connection and may also comprise a power supply means adapted to provide electrical power to the device. For instance the data transfer means may be a USB (Universal Serial Bus) cable. However, the device may have its own, independent power supply, such as a battery or a power cable connected to the electrical mains supply, particularly when the data transfer means is a wireless means. A device wherein the data transfer means is a wireless means is preferred, such as a Bluetooth™ connection, WiFi™ connection, mobile connection or any other suitable means whereby data may be transferred between the device and a local or remote computer without a hard-wired connection. This leads to less problems of tangled wires when dealing with patients, leads to less anxiety of shock for the patient, and allows the device to be easily removed for cleaning (e.g. of electrodes) without requiring disconnection of a data transfer cable. The use of a wireless connection also allows for the device to be slipped easily under the shirt or blouse of a sitting patient, avoiding the need for undressing, lying down, or employing a chaperone for female patients with a male doctor.

In the method of the invention, the further step of analysing and indicating whether the electrocardiographic data for the patient shows atrial fibrillation or atrial flutter may also be taken. This may be carried out by visual assessment of the electrocardiographic data on a display means, or in printed form, but is preferably carried out by using a software program to analyse the data to look for signal frequencies in the different leads corresponding to atrial fibrillation and/or atrial flutter. This initial assessment could be carried out immediately after the ECG data has been acquired, for instance on a computing means within the device itself, or on a local computing means connected to the device of the invention. This would allow for immediate further action to be taken in the event that the analysis of the data indicated signals corresponding to atrial fibrillation or atrial flutter.

The method of the invention allows for electrocardiographic data to be obtained from a patient without requiring removal of clothing from the patient's upper body. This is because of the small size of the device of the invention, which can thus be used to obtain ECG signals by placing it on the thoracic region of a patient either through a small aperture in a shirt (formed by opening one or two buttons say), or under a shirt or blouse. The device may suitably be provided with a recess, which allows the device to be placed on the thoracic skin of a female patient wearing a brassiere whereby the brassiere does not need to be removed or loosened. Typically, the method of the invention will be carried out on a seated or standing patient in the consulting room of a health professional, such as a doctor, nurse or consultant. In a preferred form of the method, a local computing means will be present, and in communication with the device of the invention, whereby an identified electrocardiographic dataset for the patient may be stored on the local computing means. The health professional will suitably include data to identify the patient. This data may them be optionally transmitted to a computing means at a remote location, for instance a database held on central server where it may be accessible by other health professionals. It may, for instance, be e-mailed directly to a consultant cardiologist for further analysis and/or diagnosis.

The device may, for instance, include a wireless telephony means such that it can act as a mobile telephone in connection with a mobile telephone network. In this case, electrocardiographic data, once acquired, could be sent to a remote location by means of the mobile telephone network, thus allowing it's use by paramedics for gaining rapid electrocardiographic data for transmission to a remote location.

A specific embodiment of the present invention will now be described, by way of example only, with reference to the accompanying drawing in which:

FIG. 1 shows a perspective view of an embodiment of a device according to the first aspect of the invention.

The device has a handle 5 of similar shape to a telephone receiver, such that the handle 5 may be firmly gripped by a hand to hold the device. A trigger 6 acts as an actuating means. Electrodes 11,12 are positioned on the surface of a first electrode housing 15 which is a silicone gel-filled pad having a rubber surface and further electrodes 13, 14 are positioned on the surface of a second electrode housing 16 which is also a silicone gel-filled pad having a rubber surface. The two electrode housings are separated by a gap 7 having a width W. The device has a cable 8 to allow it to be connected to a computer via a USB (Universal Serial Bus) port.

In use, a patient is seated in a medical professional's consulting room close to a personal computer including a display screen, and the screen is positioned such that it is visible by the medical professional whilst the medical professional positions the device on the patient's thoracic skin. The personal computer runs a program, which is in communication with the device via the cable 8. The device is held by the medical professional using the handle 5 and the electrodes 11, 12, 13, 14 are placed on the thoracic skin of the seated patient (without removing the clothes or underwear of the patient—the patient simply needs to open a few buttons on a shirt or blouse or the device can be positioned under a loose shirt) with electrodes 11, 12 uppermost on the patient's breast and with electrodes 13, 14 situated near the centre of the patient's sternum. The gap 7 is positioned such that the front of an adult female patient's brassiere will pass through the gap 7 and so does not need to be removed.

Signals are acquired between the electrodes and transmitted to the personal computer by the USB cable 8. Six channels of ECG signal (I, II, III, aVr, aVI, aVf) are obtained by suitable vectorial combination of the signals between pairs of electrodes, using the program running on the personal computer. The computer program running on the medical professional's personal computer displays the six channels graphically on the display screen. The medical professional can then reposition the device whilst gripping the handle 5 in order to obtain good signals, as shown on the display screen. The deformable gel pads of the first 15 and second 16 electrode housings allows the electrodes 11, 12,13,14 to be pressed firmly into the patients thoracic skin such that the electrodes may orient to give good contact. Once good signals have been achieved, the trigger 6 is pressed by the medical professional to initiate capturing the electrocardiographic signals over a predetermined time period to form an electrocardiographic dataset, which is transmitted to and stored on the personal computer by the program. Data identifying the patient is then typed into the program by the medical professional, and this is stored with the ECG data to form an identified electrocardiographic dataset.

The program may also analyses the dataset and indicate to the medical professional whether the data shows atrial fibrillation or atrial flutter, in which case it flags to the medical professional that the data is to be transmitted to a consultant cardiologist for further analysis.

It will be appreciated that numerous modifications to the above described embodiment may be made without departing from the scope of the invention as defined in the appended claims. For example, the device itself may include a small display means, or rather than a cable data transfer means 8, the device may be connected to the personal computer by a wireless interface in which case a power supply such as batteries may be needed within the device. Rather than a medical professional gripping and placing the device, this could be done by the patient themselves.

The described and illustrated embodiments are to be considered as illustrative and not restrictive in character, it being understood that only the preferred embodiments have been shown and described and that all changes and modifications that come within the scope of the inventions as defined in the claims are desired to be protected. It should be understood that while the use of words such as "preferable", "preferably", "preferred" or "more preferred" in the description suggest that a feature so described may be desirable, it may nevertheless not be necessary and embodiments lacking such a feature may be contemplated as within the scope of the invention as defined in the appended claims. In relation to the claims, it is intended that when words such as "a," "an," "at least one," or "at least one portion" are used to preface a feature there is no intention to limit the claim to only one such feature unless specifically stated to the contrary in the claim. When the language "at least a portion" and/or "a portion" is used the item can include a portion and/or the entire item unless specifically stated to the contrary.

What is claims is:

1. A hand-held device for acquiring electrocardiographic signals from a patient, comprising:
    a handle constructed and arranged for manual gripping of the device;
    an electrode array comprising four electrodes adapted for placement on a thoracic region of the patient whereby electrical contact may be made with mid-anterior thoracic skin of the patient for acquiring electrocardiographic signals through the four electrodes; and
    a first electrode housing carrying a first pair of the four electrodes and a second electrode housing carrying a second pair of the four electrodes,
    wherein each electrode is spaced from 4 cm to 20 cm from each adjacent electrode,
    wherein the first and second electrode housings are constructed and arranged to be mutually spaced to provide a gap therebetween, and
    wherein the gap is arranged to provide a void having a width of at least 1 cm and a depth of at least 1 cm when the four electrodes are positioned on said mid-anterior thoracic region of said patient.

2. The device of claim 1, wherein one or more of the electrodes is oriented or orientable with respect to the hand-held device whereby contact with said mid-anterior thoracic region of said patient may be optimized.

3. The device of claim 1, wherein all of the electrodes are orientable with respect to the device.

4. The device of claim 1, wherein one or more electrode is pivotally mounted.

5. The device of claim 1, wherein one or more electrode is positioned on a surface of a deformable pad.

6. The device of claim 5, wherein the deformable pad comprises a polymeric skin holding a silicone gel.

7. The device of claim 1, wherein the gap is arranged to permit placement of the four electrodes onto said mid-anterior thoracic region of said patient whilst said patient is wearing a brassiere.

8. The device of claim 1, wherein the four electrodes of the electrode array are positioned substantially at the vertices of a quadrilateral.

9. The device of claim 1, wherein the electrodes comprise a gold surface arranged to make electrical contact with said patient's mid-anterior thoracic skin.

10. The device of claim 1, further comprising an actuating means adapted to initiate capture of electrocardiographic signals over a predetermined time period onto a data storage means as an electrocardiographic dataset.

11. The device of claim 10, wherein the electrocardiographic dataset comprises six channels.

12. The device of claim 10, wherein the device comprises the data storage means.

13. The device of claim 1, further comprising a display means adapted to display instantaneous electrocardiographic signals from said patient.

14. The device of claim 1, further comprising a data transfer means for transferring the electrocardiographic signals or an electrocardiographic dataset to a first computing means.

15. The device of claim 14, wherein the data transfer means comprises a power supply means adapted to provide electrical power to the device.

16. The device of claim 14, wherein the data transfer means is a wireless means.

17. The device of claim 8, wherein a central portion between the first and the second electrode housings is devoid of electrodes.

18. An apparatus comprising a hand-held device for acquiring electrocardiographic signals from a patient, a display means, an actuating means, a data transfer means, a data storage means, a computer program and a computing means, wherein:
    the hand-held device comprises a handle constructed and arranged for manual gripping of the device and an electrode array comprising four electrodes adapted for placement on a thoracic region of said patient whereby electrical contact may be made with mid-anterior thoracic skin of said patient for acquiring electrocardiographic signals through the four electrodes,
    the display means is adapted to display the electrocardiographic signals from said patient, the actuating means is adapted to initiate capture of electrocardiographic signals over a predetermined time period onto the data storage means as an electrocardiographic data set, data transfer means is arranged to transfer electrocardiographic signals or the electrocardiographic data set from the hand-held device to the computing means, and the computer program is adapted to run on the computing means, the computer program including a set of instructions that when executed by the computing means causes the computing means to perform operations to acquire and manipulate the electrocardiographic data set from said patient and to add patient identification data to the electrocardiographic data set to form an identified electrocardiographic data set.

19. The apparatus of claim 18, further comprising means for transmitting the identified electrocardiographic dataset to a second computing means.

20. The apparatus of claim 18, wherein the electrocardiographic dataset comprises six channels.

21. The apparatus of claim 18, further comprising means for analysing and indicating whether the electrocardiographic data for the patient comprises features indicative of atrial fibrillation or atrial flutter.

22. The apparatus of claim 18, wherein the hand-held device is shaped to retrieve cardiac signals from the patient without requiring removal of clothing from the patient's upper body.

23. The apparatus of claim 18, wherein the actuating means is located on the hand-held device.

24. The apparatus of claim 18, further comprising means for assessing quality of the electrocardiographic signal prior to initiating capture of the electrocardiographic signals.

25. The apparatus of claim 23, wherein the actuating means comprises a finger-operated trigger located on the handle of the hand-held device.

26. The apparatus of claim 18, wherein a first pair and a second pair of electrodes are arranged to be mutually spaced to provide a gap therebetween;

wherein the gap is arranged to permit placement of the first pair of electrodes on an upper mid-anterior thoracic region and the second pair on a lower mid-anterior thoracic region;

wherein the gap is devoid of electrodes; and wherein a portion of the hand-held device adjacent the gap is sufficiently arcuate to accommodate continued wearing of a brassiere by the patient during acquisition of electrocardiographic signals through the four electrodes.

27. The apparatus of claim 18, wherein the display means displays electrocardiograph signal strength and stability so that a user can ensure that a stable, strong signal is being acquired prior to initiating capture of the electrocardiograph signals.

\* \* \* \* \*